United States Patent [19]

Quemada et al.

[11] Patent Number: 5,349,128
[45] Date of Patent: Sep. 20, 1994

[54] CUCUMBER MOSAIC VIRUS COAT PROTEIN GENE

[75] Inventors: Hector D. Quemada; Jerry L. Slightom, both of Kalamazoo, Mich.; Dennis Gonsalves, Geneva, N.Y.; Chris Kearney, Lake Alfred, Fla.

[73] Assignee: The Upjohn Company, Kalamazoo, Mich.

[21] Appl. No.: 10,423

[22] Filed: Jan. 28, 1993

Related U.S. Application Data

[63] Continuation of Ser. No. 655,435, Feb. 19, 1991, abandoned, which is a continuation of Ser. No. 234,404, Aug. 19, 1988, abandoned.

[51] Int. Cl.$^5$ ............ A01H 1/04; C12N 15/00; C12N 5/00; C07H 21/04
[52] U.S. Cl. .................. 800/205; 435/70.1; 435/172.3; 435/240.4; 435/252.3; 435/320.1; 536/23.72; 800/DIG. 18; 800/DIG. 40
[58] Field of Search .............. 536/23.72; 435/172.3, 435/252.3, 240.4, 320.1, 70.1; 800/205, DIG. 18, DIG. 40

[56] References Cited

PUBLICATIONS

Namba et al. 1991, Gene 107:181–188.

*Primary Examiner*—David T. Fox
*Attorney, Agent, or Firm*—Sidney B. Williams, Jr.

[57] ABSTRACT

The coat protein gene of cucumber mosaic virus strain WL (CMV-WL), the method of preparing it, its use to prepare transgenic plants and transgenic plants containing it are provided.

6 Claims, No Drawings

CUCUMBER MOSAIC VIRUS COAT PROTEIN GENE

CROSS REFERENCE TO RELATED APPLICATIONS

The present application is a continuation application of Ser. No. 07/655,435, filed Feb. 19, 1991, now abandoned; which is the National Phase of International application Ser. No. PCT/US89/03288, filed Aug. 2, 1989; which is a continuation of U.S. patent application Ser. No. 07/234,404, filed Aug. 19, 1988, now abandoned.

FIELD OF INVENTION

This invention relates to a coat protein gene of cucumber mosaic virus strain WL (CMV-WL). More specifically the invention relates to a process for preparing said gene as well as its incorporation into a transfer vector and to its use to produce transformed plant cells and transformed plants which are resistant to CMV viral infections.

BACKGROUND OF THE INVENTION

Cucumber mosaic virus (CMV) is a single-stranded (+) RNA plant virus which has a functionally divided genome. The virus genome contains four RNA species designated RNAsl-4;3389 nucleotides (nt), 3035 nt, 2193 nt and 1027 nt, respectively (Peden and Symons, 1973; Gould and Syrnons, 1982; Rezaian et al., 1984; Rezaian et al., 1985). Only RNAsl-3 are required for infectivity (Peden and Symons, 1973) because the coat protein, which is encoded by RNA 4, is also encoded by RNA 3. Translations of CMV RNAs yield a 95KDal polypeptide from RNA 1, a 94kDal polypeptide from RNA 2, (Gordon et al., 1983) and two polypeptides from RNA 3: its 5' end encodes a 35KDal polypeptide, and its 3' end encodes a 24.5kDal polypeptide (Gould and Symons, 1982). The 24.5kDal polypeptide is identical to dial encoded by RNA 4 and is the coat protein.

Several strains of cucumber mosaic virus have been classified using serology (Devergne and Cardin, 1973, 1975), host range (Marrow et al. 1975), peptide mapping (Edwards and Consalves, 1983), and nucleic acid hybridization (Piazzola et at., 1979; Gonda and Symons, 1978). These CMV strains can be divided into two groups designated S and WT. The genome of the CMV-Q strain has been completely sequenced (Rezaian et al., 1984, 1985; Gould and Symons. 1982; Davies and Symons, 1988). The Q strain is a member of the S group, which consists of three members. The WT group is Iraown to contain at least 17 members. From nucleotide sequence analysis and comparisons of the coat protein genes from CMV-C and CMV-WL (Quemada et al, manuscript in preparation; see Chart 1) we have determined that the C strain belongs to the WT group while the WL belongs to the S group. The nucleotide and amino acid sequences of the coat protein genes from strains C and WL differ by 22.7% and 16%, respectively (see charts 2 and 3).

As has been shown for several viruses [tobacco mosaic virus (Powell-Abel et at., 1986), alfalfa mosaic virus (Loesch-Fries et al., 1987; Tumer et al., 1987), cucumber mosaic virus (Cuozzo et al., 1988; Quemada and Slightore, in preparation), and potato virus X (Hemenway et al., 1988)]expression of the coat protein in transgenie plants results in a plant which is resistant to infection by the respective virus. However, whether this engineered cross-protection will extend to all strains of a particular virus has not been determined. The two CMV groups appear to differ in their coat protein gene by about 16%, thus it is possible that the expression of both virus coat proteins may be needed to ensure engineered cross-protection against CMV infections which could be expected under field conditions.

The CMV coat protein gene does not contain the signals necessary for its expression once transferred and integrated into a plant genome. It must be engineered to contain a constitutive promoter 5' to its translation initiation codon (ATG) and a poly(A) addition signal (AATAAA) 3' to its translation termination codon. Several promoters which function in plants are available, but we believe that the best promoters is the 35S constitutive promoters from cauliflower mosaic virus (CaMV). The poly (A) signal can be obtained from the CaMV 35S gene or from any number of well characterized plant genes, i.e. hopaline synthase (Bevan et al.,1983), octopine synthase (Depicker et at., 1982), and the bean storage protein gene phaseolin (Slightore, et at., 1983). The constructions are similar to that used for the expression of the CMV-C coat protein in PCT Patent Application PCT/U.S. Pat. No. 88/04321, published on Jun. 29, 1989 as WO 89/05858, claiming the benefit of U.S. Ser. No. 135,591, filed Dec. 21, 1987, now abandoned, entitled "Cucumber Mosaic Virus Coat Protein Gene", the essential pans which are herein incorporated by reference.

INFORMATION DISCLOSURE

Plants that are resistant to virus diseases and methods for producing them are described in EP 223,452.

Information contained in the following references also describe materials, procedures, and results of interest for engineering virus coat protein genes for expression in transgenie plants.

An, G., et at. (1985) "New Cloning Vehicles for Transformation Of Higher Plants". EMBO J. 4:277–284.

An. G. (1986) "Development of plant promoter expression vectors and their use for analysis of differential activity of hopaline synthase promoter in transformed tobacco cells". Plant Physiol. 81:86–89.

Bevan, M., et al. (1983) "Structure and transcription of the nopaline synthase gene region of T-DNA". Nucleic Acids Research 11:369–379.

Cuozzo, M., et al. (1988) "Viral protection in transgenie tobacco plants expressing the cucumber mosaic virus coat protein or its antisense RNA". Bio/tech. 6:549–557.

Davies. C. and Symons, R. (1988) "Further implications for the evolutionary relationships between tripartite plant viruses based on cucumber mosaic virus RNA 3. Virology 164 :in press.

Depicker, A., et al. "Nopaline synthase: transcript mapping and DNA sequence". J. Mol. Appl. Genet. 1:561–573.

Devergne, J. and Cardin, L. (1973) "Contribution a l'etude du virus de la mosaique du concombre (CMV). IV. Essai de classification de plusieurs isolats sur la base de leur structure antigenique". Arm. Phytopathol. 5:409–430.

Devergne, J. and Cardin, L. (1975) "Relations serologiques entre cucumovirus (CMV, TAV, PSV)" Arm. Phytopathol. 7:255–276.

Dodds, J. A., et al. (1985) "Cross protection between strains of cucumber mosaic virus: effect of host and type of inoculum on accumulation of virions and double-stranded RNA of the challenge strain". Virology 144:301-309.

Edwards, M. and Consalves, D. (1983) "Grouping seven biologically defined isolates of cucumber mosaic virus by peptide mapping". Phytopathology 73:1117-1120.

Gonda, T. and Symons, R. (1978) "The use of hybridization analysis with complementary DNA to determine the RNA sequence homology between strains of plant viruses: Its application to several strains of cucumoviruses". Virology 88:361-370.

Gonsalves, D., et al. (1982) "Tomato whiteleaf: The relation of an apparent satellite RNA and cucumber mosaic virus". Phytopathology 72:1533-1538.

Gordon. K., et al. (1982) "Highly purified cucumber mosaic virus-induced RNA-dependent RNA polymerase does not contain any of the full length translation products of the genomic RNAs". Virology 123:284-295.

Gould. A. and Symons, R. (1982) "Cucumber mosaic virus RNA 3. Determination of the nucleotide sequence provides the amino acid sequence of protein 3A and vital coat protein". Eur. J. Biochem. 126:217-227.

Hemenway, C., et at. (1988) "Analysis of the mechanism of protection in transgenie plants expressing the potato virus X coat protein or its antisense RNA". EMBO J. 7:1273-1280.

Hepburn, A., et al. (1985) "The use of pNJ5(R.)0as an intermediate vector tier genetic manipulation of ARm-bacterium Ti-plasmids". J. General Microbio. 131:2961-2969.

Loesch-Fries, S., et al. (1987) "Expression of alfalfa mosaic virus RNA 4 in transgenie plants confers virus resistance". EMBO J. 6:1845-1851.

Marrou, J.. et al. (1975) "Caracterisation de douze souches du VMC par leurs aptitudes pathogenes: Tentative de classification". Meded. Fac. Landbouwwet. Rijks. Univ. Gent. 40:107-122.

Peden, K. and Symons, R. (1973)"Cucumber Mosaic Virus Contains a functionally divided genome". Virology 53:487492.

Piazzola, P., et al. (1979) "Nucleic acid homologies of eighteen cucumber mosaic virus isolates determinecl by competition hybridization". J. Gen. Virol. 45:361-369.

Pietrzak. M., et al. (1986) "Expression in plants of two bacterial antibiotic resistant genes after protoplast transformation with a new plant expression vector". Nuc. Acids Res 14:5857-5868.

Polites, H. and Marotti, K. (1986)"A step-wise protocol for eDNA synthesis" Biotechniques 4:5 14–520.

Powell-Abel, P., et al. (1986) "Delay of disease development in transgenie plants that express the tobacco mosaic virus coat protein gene". Science 232:738-743.

Rezaian, M., et al. (1984) "Nucleotide sequence of cucumber mosaic virus RNA 2 reveals a translation product significantly homologous to corresponding proteins of other viruses". Eur. J. Biochem. 143:277-284.

Rezaian, M., et al. (1985) "Nucleotide sequence of cucumber mosaic virus RNA 1. Presence of a sequence complementary to pan of the viral satellite RNA and homologies with other viral RNAs. Eur. J. Blochem. 150:331-339.

Slightore, J., et al. (1983) "Complete nucleotide sequence of a French bean storage protein gene:Phaseolin". Proc. Natl. Acad. Sci. U.S.A. 80:1897-1901.

Turner, N., et al. (1987) "Expression of alfalfa mosaic virus coat protein gene confers cross-protection in transgenie tobacco and tomato plants". EMBO J. 6:1181-1188.

Vilaine, F. and Casse-Delbart, F. (1987) "Independent induction of transforaged rooks by the TL and TR region of the Ri plasmid of agropine type *Agrobactedum rhizogenes*". Mol. Gert. Genet. 206:17-23.

SUMMARY OF THE INVENTION

This invention provides: The coat protein gene from the WL strain of cucumber mosaic virus (CMV-WL).

A plant transformation vector comprising the coat protein gene from CMV-WL. the promoter of the 35S gene of cauliflower mosaic virus and the polyadenylation signal of cauliflower mosaic virus 35S gene.

A bacterial cell containing a plant transformation vector comprising the coat protein gene from CMV-WL, the 35S promoter of cauliflower mosaic virus and the polyadenylation signal of the cauliflower mosaic virus 35S gene.

A transformed plant cell containing the coat protein gene from CMV-WL, the cauliflower mosaic virus 35S promoter and the polyadenylation signal of the cauliflower mosaic virus gene.

A plant comprising transformed cells containing the coat protein gene of CMV-WL, the cauliflower mosaic virus 35S promoter and the polyadenylation signal of the cauliflower mosaic virus gene. Transformed plants of this invention include beets, citrus fruit, corn, cucumber, peppers, potatoes, soybean, squash and tomatoes. Especially preferred are members of the cucurbitaceae (squash, cucumber, i.e.,) and solanaceae (peppers, tomatoes, i.e.) family.

A process for producing virus-resistant plants comprising propagating a plant expressing the coat protein gene from the WL strain of cucumber virus. Especially preferred is the process for producing members of the cucurbitacaea and solanacaea families.

DESCRIPTION OF THE PREFERRED EMBODIMENT

Charts 1 to 5 are set forth to illustrate the constructions of this invention. Certain conventions are used to illustrate plasmids and DNA fragments as follows:

(1) The single line figures represent both circular and linear double-stranded DNA.

(2) Asterisks (*) indicate that the molecule represented is circular. Lack of an asterisk indicates the molecule is linear.

(3) Junctions between natural boundaries of functional components are indicated by vertical lines along the horizontal lines.

(4) Genes or functional components are indicated.

(5) Distances between genes and restriction sites are not to scale. The figures show the relative positions only unless indicated otherwise.

Most of the recombinant DNA methods employed in practicing the present invention are standard procedures, well Iraown to those skilled in the art, and described in detail, for example, EP-223452 which is incorporated herein by reference. Enzymes are obtained from commercial sources and are used according to the vendor's recommendations or other variations known to the art. Reagents, buffers, and culture conditions are also known to those in the an. General references containing such standard techniques incorporated herein by reference include the following: R.Wu, ed. (1979) *Methods in Enzymology* Vol.68; J. H. Miller (1972) *Experiments in Molecular Genetics*; T. Maniatis et at.(1982) *Molecular Cloning: A Laboratory Manual*; and D. M. Glover, ed. (1985) *DNA Cloning* Vol II; S. B. Gelvin and R. A. Schilperoon, eds. *Introduction, Expression, and Analysis of Gene Products in Plants.* Example 1 Isolation of CMV RNAs Cucumber mosaic virus strain WL (CMV-WL) was propagated in tobacco plants (cv. Havana 423) mid RNA was isolated by standard methods, for example by the method of Lot et al. (Annals of Phytopathology 4:25, 1972). RNA 3 was separated from other CMV-WL RNAs by sucrose density gradient centrifugation.

Example 2 Cloning of CMV-WL RNA3

(a) Synthesis of double-stranded eDNA3

Purified CMV-WL RNA3 was polyadenylated in order to provide a site for the annealing of an oligo dT primer. The reaction buffer was as follows: 5 μl, 1 M Tris pH 7.9; 1 μl, 1 M MgCl2; 2.5 μl, 0.1 M MnCl2; 5 μl, 5 μ NaCl; 0.5 μl, 100 mM ATP; 18 μl, 2.8 mg/ml bovine serum albumin. 3.2 μl of this buffer were mixed with 2 μg of CMV-WL RNA3. 3.8 μl H2O and 1 μl of poly-A polymerase were added, and the reaction mixtures were incubated at 37° C. for 10 minutes.

The resulting polyadenylated RNA was used in the eDNA synthesis protocol of Polites and Marotti (Biotechniques 4:5 14, 1986), except that 0.75 mM KCI was used instead of 50 mM NaCl, and 130 uCi/100 μl 32P-dCTP was used instead of 10–50 uCi/100 μl.

After ds-cDNA was synthesized, it was purified by G-100 column chromatography, precipitated with ethanol, and suspended in 20 μl of IX Eco R1 methylase buffer (100 nM NaCl, 100 mM Tris-HCL pH 8.0, 1 mM EDTA,80 μM S-adenosyl methionine, 100 μg/ml bovine serum albumin). After removal of a 2 μl aliquot for subsequent gel analysis, an additional 1 μl of 32 mM S-adenosyl methionine was added to the reaction mixture mix, and 1 μl (20 units) of Eco RI methylase. The reaction was incubated at 37° C. for 30 minutes and stopped by incubation at 70° C. for 10 minutes.

Two μl were removed from the above reaction, and 1 μl (5 units) of E. coli DNA polymerase I klenow fragment was added. The reaction was incubated at 37° C. for 10 minutes, then extracted with phenol/clfiorofonn before precipitating with ethanol. The pellet was washed in 70% ethanol, then in 70% ethanol/0.3 M sodium acetate.

The pellet was dried and resuspended in 8 μl 0.5 μg/μl phosphorylated Eco RI linkers (available from Collaborative Research, Inc, 128 Spring Street, Lexington, Mass. 02173). One μl 10X ligase buffer (800 mM Tris-HCl pH 8.0, 200 mM MgCl2, 150 mM DTT, 10 mM ATP) and 1 μl of T4 DNA ligase (4 unils/μl) were added, and the reaction was incubated overnight at 15° C.

The ligation reaction was then stopped by incubation at 65° C. for 10 minutes. Sixty μl of water. 10 μl of 10X Eco RI salts(900 mM Tris pH 8.0, 100 mM MgC12, 100 mM NaC1), and 10 μl of EcoRI (10 units/laD were added, and the reaction was incubated at 37° C. for 1 hr (a 5 μl aliquot was removed at the beginning for subsequent gel analysis). The reaction was stopped by phenol/chlorofonn and chlorofonn extraction. A 5 μl aliquot was removed for gel analysis, and half of the remainder was frozen for future use. The other half was purified by G-100 column chromatography. The G-100 fractions containing the eDNA were concentrated by butanol extraction, precipitated with ethanol, and resuspended in 10 μl of H2O. After removing 3 μl for subsequent analysis, 1 μl lambda gtll or lambda Zap arms (available from Stratagene Co., 3770 Tandy St, San Diego, Calif. 92121), 1 μl of 10X ligase buffer, and 1 μl T4 DNA ligase were added, and file reaction was incubated at 15° C. overnight.

The resulting ligated lambda gtll or Zap/cDNA molecules were packaged according to the procedure recommended by the manufacturer of the packaging extract (Gigapack plus, also from Stratagene). This yielded recombinant lambda phage, which were plated according to methods known to those skilled in the art.

Lambda clones containing the coal protein gene were identified by hybridization with radioactively labelled single-stranded eDNA from purified RNA4 of CMV-WL. This RNA4 single-stranded cDNA was synlhesized Its follows: RNA 4 molecules were polyadenylated as described above for CMV-WL RNA3, except that 5.8 μg RNA4 was used. First strand synthesis was as described by Polites and Marotli (Biotechniques 4:5 14, 1986) except that non-radioactive dCTP was not included. Instead, 260 uCi/100 μl of radioactive dCTP was used.

The labelled single-stranded eDNA was purified by P6 column chromatography and used to probe replicate filters lifted front the lambda phage plates mentioned above. The single-stranded cDNA hybridized with DNA from several phage clones, indicating that they contained at least a part of the CMV-WL coat protein gene. Several of these lambda clones were grown, and DNA from them was isolated according to methods known to those skilled in the art.. In particular, lambda clone WL3Z8 was isolated and its insert of about 2.0kb contains all of CMV-WL RNA3 except the 5'-193 bp.

Example 3 Construction of a pUCI9 Clone containing the CMV-WL coat protein gene

The EcoRI fragments from lambda clone WL3Z8 were transferred t.o the plasmid vector, pUC19 (available from Bethesda Research, P.O. Box 6009, Gaithersburg, Md. 20877), using standard methods to obtain clone pWL3ZS.1. The EcoRI cloned fragments in pUC19 were then sequenced by the technique described by Maxam and Gilbert (*Methods in Enzymology* 65:499, 1980). Based on this information the complete sequence of the CMV-WL coat protein gene was determined and this is shown in Chart 1. Additional sequencing showed that clone pWL3ZS.1 contains all but the 5'193 bp of the CMV-WL RNA3 molecule, as determined by comparison with the complete sequence of CMV-Q RNA3 (Davis and Symons, 1988, *Virology* 164:in press). The nucleotide and amino acid sequence oi: CMV-WL and CMV-C differ by 22.7% (chart 2) and 16% (chart 3), respectively.

Example 4 Construction of a micro T-DNA plasmid containing a a plant-expressible CMV-WL coat protein gene with the CaMV 35S polyadenylation signal In order to attach the CaMV 35S promoter and polyadenylation signal, a fragment extending from an ApaI site (located within the intergenie region of RNA3) to an EcoRI site (attached during the cloning experinent) was removed from lambda clone WL3Z8 and ligated into the multiple cloning site of the vector pDH51 (Pietrzak et at., 1986) (available from Thomas Hohn, Friedrich Miescher Institute, P.O. Box 2543, CH-4002, Basel, Switzerland). This was accomplished by complete digestion with ApaI and a partial digest with EcoRI of WL3Z8, creating a blunt-ended molecule out of the appropriate ApaI to EcoRI 1090 bp fragment (using mung bean nuclease), followed by ligating it into the SmaI site of pDH51 (see Chart 4). This clone, designated pDH51/CPWL, was sequenced by the Maxam-Gilbert technique to confirm its suitability for expression in plants.

The plant expressible coat protein gene was then moved into a vector suitable for Agrobacterium-mediated gene transfer. Following partial digestion with EcoRI, the EcoRI to EcoRI fragment of about 1.9kb was removed from pDH51/CPWL and placed into the EcoRI site of the plasmid, pUC1813 (available from Robert Kay, Dept. of Chemistry, Washington State University, Pullman, Wash.), creating the plasmid pUC 1813/CPWL. A 1.9 kb fragment containing this plant expressible CMV-WL coat protein gene was removed by partial HindIII digestion and ligated into the HindIII site of the vector, pGA482 (An, 1986) (available from Gynehung An, Institute of Biological Chemistry. Washington State University). The plasmid pGA482 was previously modified to contain the plant expressible β-glucuronide gene as described in WO 89/05858, incorporated above, and the modified plasmid is referred to as pGA482/G. After cloning the expression cassette the plasmid was designated pGA482/CPWL/G (see Chart 5).

This plasmid, or its derivatives, can be transferred into Agrobacterium strains A208, C58. LBA4404, C58Z707, A4RS, A4RS(pRiB278b) and others using methods known to those skilled in the art. Strains A208, C58, LBA4404, and A4RS are available from ATCC, 12301 Parklawn Drive, Rockville, Md. A4RS(pRiB278b) is available from Dr. F. Casse-Delbart, C.N.R.A., Routede Saint Cyr, F78000, Versailles, France. C58Z707 is available from Dr. A. G. Hepburn. University of Illinois, Urbana, Ill. Agrobactefiurn-mediated transfer of the plant expressible CMV-WL coat protein gene is done using the procedures known to those skilled in the an or by using the methods described in a U.S. patent application Ser. No. 135,655 filed Dec. 21, 1987 entitled "Agrobacterium Mediated Transformation of Germinating Plant Seeds", which application was reftled as PCT application PCT/US88/04464, and published on 29 June 1989 as WO 89/05859, the essential pans which are herein incorporated by reference. Transfer of this gene into plant cell can also be accomplished using other methods, such as, direct DNA uptake (Paszkowski, et al., EMBO J., 1984, 3:2717), microinjection (Crossway, et al., Mol. Gert. Genet. 202: 179), electropotation (From et al., Proc. Natl. Acad. Sci. U.S.A. 82:5824), or high-velocity microprojectiles (Klein, et al., Nature 327:70).

Chart 1
Nucleotide and Amino Acid Sequence of CMV-WL Coat Protein Gene

```
      ATGGACAAATCTGGATCTCCCAATGCTAGT
1     ----------+----------+---------+
      Met Asp Lys Ser Gly Ser Pro Asn Ala Ser
                                             AGAACCTCCCGGCGTCGTCGCCCGCGTAGA
                                             ----------+----------+---------+  60
                                             Arg Thr Ser Arg Arg Arg Arg Pro Arg Arg

GGTTCTCGGTCCGCTTCTGGTGCGGATGCA
61    ----------+----------+---------+
      Gly Ser Arg Ser Ala Ser Gly Ala Asp Ala
                                             GGGTTGCGTGCTTTGACTCAGCAGATGCTG
                                             ----------+----------+---------+  120
                                             Gly Leu Arg Ala Leu Thr Gln Gln Met Leu

AAACTCAATAGAACCCTCGCCATTGGTCGT
121   ----------+----------+---------+
      Lys Leu Asn Arg Thr Leu Ala Ile Gly Arg
                                             CCCACTCTTAACCACCCAACCTTCGTGGGT
                                             ----------+----------+---------+  180
                                             Pro Thr Leu Asn His Pro Thr Phe Val Gly

AGTGAAAGCTGTAAACCCGGTTACACTTTC
181   ----------+----------+---------+
      Ser Glu Ser Cys Lys Pro Gly Tyr Thr Phe
                                             ACATCTATTACCCTGAAACCGCCTGAAATT
                                             ----------+----------+---------+  240
                                             Thr Ser Ile Thr Leu Lys Pro Pro Glu Ile

GAGAAGGTTCATATTTTGGTAGAAGGTTG
241   ----------+----------+---------+
      Glu Lys Gly Ser Tyr Phe Gly Arg Arg Leu
                                             TCTTTGCCAGATTCAGTCACGGACTATGAT
                                             ----------+----------+---------+  300
                                             Ser Leu Pro Asp Ser Val Thr Asp Tyr Asp

AAGAAGCTTGTTTCGCGCATTCAAATCAGG
301   ----------+----------+---------+
      Lys Lys Leu Val Ser Arg Ile Gln Ile Arg
                                             GTTAATCCTTTGCCGAAATTTGATTCTACC
                                             ----------+----------+---------+  360
                                             Val Asn Pro Leu Pro Lys Phe Asp Ser Thr

GTGTGGGTTACAGTTCGGAAAGTACCTTCA
```

-continued
Chart 1
Nucleotide and Amino Acid Sequence of CMV-WL Coat Protein Gene

```
361 ----------+----------+----------+
    Val  Trp  Val  Thr  Val  Arg  Lys  Val  Pro  Ser
                                              T CAT CCG ATC TTT CCG TCG CCG CCA TCT CT
                                              ----------+----------+----------+ 420
                                              Ser  Ser  Asp  Leu  Ser  Val  Ala  Ala  Ile  Ser

GCT ATG TTT GGC GAT GGT AAT TCA CCG GTT
421 ----------+----------+----------+
    Ala  Met  Phe  Gly  Asp  Gly  Asn  Ser  Pro  Val
                                              T TGG TTT ATC AGT ATG CTG CGT CCG GAG TT
                                              ----------+----------+----------+ 480
                                              Leu  Val  Tyr  Gln  Tyr  Ala  Ala  Ser  Gly  Val

CAG GCC AAC AAT AAG TTA CTT TAT GAC CTG
481 ----------+----------+----------+
    Gln  Ala  Asn  Asn  Lys  Leu  Leu  Tyr  Asp  Leu
                                              T CCG AGA TGC GTG CTG ATA TCG GCG ACA TG
                                              ----------+----------+----------+ 540
                                              Ser  Glu  Met  Arg  Ala  Asp  Ile  Gly  Asp  Met

CGT AAG TAC GCC GTC CTG GTT TAC TCG AAA
541 ----------+----------+----------+
    Arg  Lys  Tyr  Ala  Val  Leu  Val  Tyr  Ser  Lys
                                              GAC GAT AAA CTA GAG AAG GAC GAG ATT GCA
                                              ----------+----------+----------+ 600
                                              Asp  Asp  Lys  Leu  Glu  Lys  Asp  Glu  Ile  Ala

CTT CAT GTC GAC GTC GAG CAT CAA CGA ATT
601 ----------+----------+----------+
    Leu  His  Val  Asp  Val  Glu  His  Gln  Arg  Ile
                                              CCT ATC TCA CGG ATG CTC CCG ACT TAG
                                              ----------+----------+-------- 657
                                              Pro  Ile  Ser  Arg  Met  Leu  Pro  Thr  End
```

Chart 2
Comparison of CMV-WL and CMV-C coat protein genes

```
CMV-WL ATGGACAAATCTGGATCTCCCAATGCTAGTAGAACCTCCCGGCGTCGTCG      60
       |||||||||||||  |||  |||·||||  || |          ||  || |||||
CMV-C  ATGGACAAATCTGAATCAACCAGTGCTGGTCGTA...ACCATCGACGTCG      47

CCCGCGTAGAGGTTCTCGGTCCG...CTTCTGGTGCGGATGCAGGGTTGC      97
       ||||||  | |||| |||  ||    |||    |||||||||        ||
       TCCGCGTCGTGGTTCCCGCTCCGCCCCCTCCTCCGCGGATGCTAACTTTA      97

GTGCTTTGACTCAGCAGATGCTGAAACTCAATAGAACCCTCGCCATTGGT    147
       | |  ||| |||||||||||| ||||| ||  || |||  ||| | ||||
       GAGTCTTGTCGCAGCAGCTTTCGCGACTTAATAAGACGTTAGCAGCTGGT    147

CGTCCCACTCTTAACCACCCAACCTTCGTGGGTAGTGAAAGCTGTAAACC    197
       |||||  ||| |||||||||||||||| || || |||||| ||||||  |||
       CGTCCAACTATTAACCACCCAACCTTTGTAGGGAGTGAACGCTGTAGACC    197

CGGTTACACTTTCACATCTATTACCCTGAAACCGCCTGAAATTGAGAAAG    247
       | |  |||||| |||||||||||||||||| || || || ||||| ||  |
       TGGGTACACGTTCACATCTATTACCCTAAAGCCACCAAAAATAGACCGTG    247

GTTCATATTTTGGTAGAAGGTTGTCTTTGCCAGATTCAGTCACGGACTAT    297
       || ||||| ||||||||||||| | || |||||||||||||||||| |||
       AGTCTTATTACGGTAAAAGGTTGTTACTACCTGATTCAGTCACGGAATAT    297

GATAAGAAGCTTGTTTCGCGCATTCAAATCAGGGTTAATCCTTTGCCGAA    347
       ||||||||||||||||||||||||||||| | ||||||||||||||||||
       GATAAGAAGCTTGTTTCGCGCATTCAAATTCGAGTTAATCCTTTGCCGAA    347

ATTTGATTCTACCGTGTGGGTTACAGTTCGGAAAGTACCTTCATCATCCG    397
       |||||||||||||||||||||  |||| || ||||| |||  || || |
       ATTTGATTCTACCGTGTGGGTGACAGTCCGTAAAGTTCCTGCCTCCTCGG    397

ATCTTTCCGTCGCCGCCATCTCTGCTATGTTTGGCGATGGTAATTCACCG    447
       |  | ||||||||||||||||||||||||||||| || ||| || ||||||
       ACTTATCCGTTGCCGCCATCTCTGCTATGTTCGCGGACGGAGCCTCACCG    447
```

-continued

Chart 2
Comparison of CMV-WL and CMV-C coat protein genes

```
GTTTTGGTTTATCAGTATGCTGCGTCCGGAGTTCAGGCCAACAATAAGTT    497
||  |||||||||||||||| || || ||||| ||  |||||||| ||  |
GTACTGGTTTATCAGTATGCCGCATCTGGAGTCCAAGCCAACAACAAACT    497

ACTTTATGACCTGTCCGAGATGCGTGCTGATATCGGCGACATGCGTAAGT    547
 | ||||  || ||  |  ||||||| |||||||  |  ||||| | ||||
GTTGTTTGATCTTTCGGCGATGCGCGCTGATATAGGTGACATGAGAAAGT    547

ACGCCGTCCTGGTTTACTCGAAAGACGATAAACTAGAGAAGGACGAGATT    597
|||||||||| ||  ||  ||||||||| |  || ||||| |||||||| |
ACGCCGTCCTCGTGTATTCAAAAGACGATGCGCTCGAGACGGACGAGCTA    597

GCACTTCATGTCGACGTCGAGCATCAACGAATTCCTATCTCACGGATGCT    647
| |||||||||  ||| |||||||  |||  |||| |||   ||||  |||
GTACTTCATGTTGACATCGAGCACCAACGCATTCCCACATCTGGAGTGCT    647

CCCGACTTAG    657
|||     |
CCCAGTCTGA    657
```

Chart 3
Comparison of CMV-WL and CMV-C coat proteins

```
CMV-WL  MDKSGSPNAS RTSRRRRPRRGSRSA. SGADAGLRALTQQMLKLNRTLAI G    49
        ||||  |    |  |||||||||||||  |||  ||   ||  ||  ||  |
CMV-C   MDKSESTS AGR. NHRRRPRRGSRSAPSS ADANFRVLSQQL SRLNKTLAAG    49

RPTLNHPTFVGSES CKPGYTFTSITLKPPEIE KGSYFGRRLSLPDSVTDY    99
        |||| ||||||||   || |||||||||||||  ||   | || ||||||| |
        RPTI NHPTFVGSERCR PGYTFTSITLKPPKIDRE SYYGKRLLLPDSVTEY    99

DKKLVSRIQIRVNPLPKFDSTVWVTVRKVPS SSDLSVAAISAMFGDGNSP    149
        ||||||||||||||||||||||||||||||  ||||||||||||| | |
        DKKLVSRIQIRVNPLPKFDSTVWVTVRKVPASSDLSVAAISAMFADGASP    149

VLVYQYAASGVQANNKLLYDLSEMRADIGDMRKYAVLVYSKDDKLEKDEI    199
        |||||||||||||||||| ||| |||||||||||||||||||| |  |||
        VLVYQYAASGVQANNKLLFDLSAMRADIGDMRKYAVLVYSKDDALETDEL    199

ALHVDVEHQRIPI SRMLPT*    219
         ||||| ||||||  |  |||
        VLHVDI EHQRIPTSGVLPV*    219
```

Chart 4
Construction of RDH 51/cpWL

```
            CMV-WL
WL3Z8  |----------------|------------------|----|
                              coat protein gene       ↑
                                                   A residues
                     └─────────────────┬──────────┘
                                       ↓
                                                      CaMV 35S
                                                      poly-A
                                                      signal
                          CMV-WL                        ↓
pDH51/CPWL |----------|----|------------------|---|---|
           CaMV              coat protein gene        ↓
           35S                                    A residues
           promoter
```

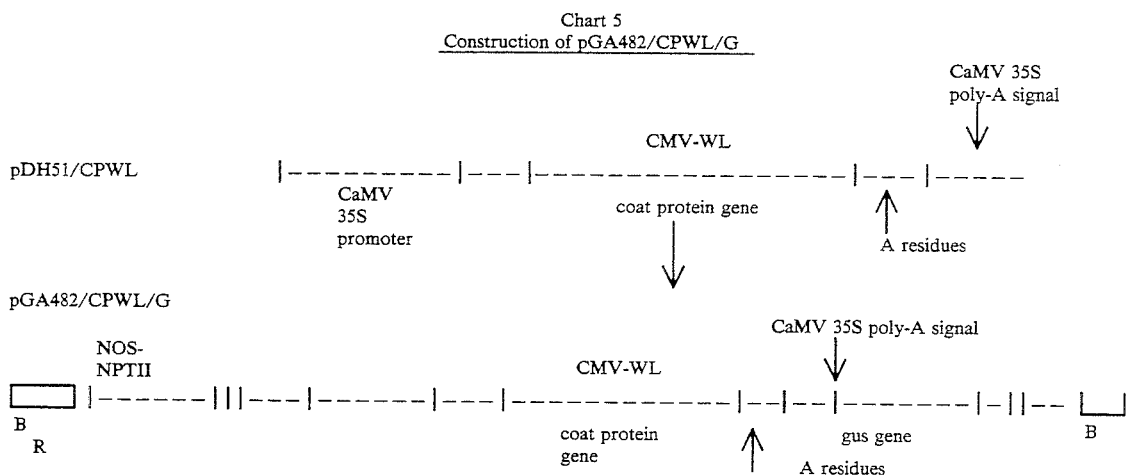

Chart 5
Construction of pGA482/CPWL/G

We claim:

1. The coat protein gene from the WL strain of cucumber mosaic virus and having the sequence shown in Chart 1.

2. A plant transformation vector comprising the coat protein gene according to claim 1, the 35S promoter of califlower mosaic virus and the polyadenylation signal of the califlower mosaic 35S gene, wherein said promoter is upstream from said CMV-WL coat protein gene 5' untranslated region; and said CMV-WL coat protein gene 5' untranslated region is upstream from a link to said polyadenylation signal of the califlower mosaic 35S gene.

3. A bacterial cell containing the plant transformation vector of claim 2.

4. A transformed plant cell containing the plant

5. A plant selected from the family cucurbitaceae comprising the transformed plant cell of claim 4.

6. A plant selected from the family solanaceae comprising the transformed plant cell of claim 4.

* * * * *